(12) United States Patent
Golden et al.

(10) Patent No.: US 8,444,417 B2
(45) Date of Patent: *May 21, 2013

(54) METHODS FOR TREATING DENTAL DISEASES, DISORDERS, AND INJURIES

(75) Inventors: William J. Golden, Boston, MA (US); Randall G. Rupp, Swanton, VT (US)

(73) Assignee: Stemnion, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/374,166

(22) Filed: Dec. 14, 2011

(65) Prior Publication Data

US 2012/0156649 A1    Jun. 21, 2012

Related U.S. Application Data

(60) Provisional application No. 61/459,859, filed on Dec. 20, 2010.

(51) Int. Cl.
| | | |
|---|---|---|
| *A61C 5/00* | (2006.01) | |
| *A61C 15/00* | (2006.01) | |
| *A61B 5/117* | (2006.01) | |
| *C07K 1/00* | (2006.01) | |
| *A61K 38/16* | (2006.01) | |
| *A61K 38/18* | (2006.01) | |

(52) U.S. Cl.
USPC ........ 433/228.1; 433/215; 433/216; 433/229; 530/350; 530/351; 530/380; 514/8.1; 514/8.2; 514/8.9

(58) Field of Classification Search
None
See application file for complete search history.

(56) References Cited

U.S. PATENT DOCUMENTS

| 8,088,732 B2 | 1/2012 | Marshall et al. |
|---|---|---|
| 2004/0019110 A1 | 1/2004 | Van Dyke et al. |
| 2005/0238589 A1 | 10/2005 | Van Dyke et al. |
| 2006/0222634 A1 | 10/2006 | Clarke et al. |
| 2007/0231297 A1 | 10/2007 | Smith et al. |
| 2008/0045575 A1 | 2/2008 | Van Dyke et al. |
| 2008/0280980 A1 | 11/2008 | Van Dyke |
| 2009/0010899 A1 | 1/2009 | Palladino et al. |
| 2009/0054339 A1 | 2/2009 | Marshall et al. |
| 2010/0080779 A1 | 4/2010 | Smith et al. |
| 2010/0129328 A1 | 5/2010 | Sing et al. |

OTHER PUBLICATIONS

Kaigler, D., et al., 2011, Expert Opin Biol 11(3):375-385.
Krayer, J.W., et al., 2009, Dent Clin North Am 54(1):13-33.
Van Dyke, T.E., 2008 J Periodontol 79(8 Suppl):1601-1608.
Barksby, H.E., et al., 2007, Clin Exp Immunol 149:217-225.
Steed, D.L., et al., 2008 ePlasty Open Access Journal of Plastic Surgery, e18.

*Primary Examiner* — Christine J Saoud
*Assistant Examiner* — Jegatheesan Seharaseyon
(74) *Attorney, Agent, or Firm* — Linda O. Palladino; Gail M. Kempler

(57) ABSTRACT

Methods for preventing, reversing, ameliorating or treating dental diseases, disorders or injuries are provided. In particular, methods for preventing, reversing, ameliorating or treating dental diseases of the gingival (gums) and bone are provided. Such methods utilize novel compositions including, but not limited to, extraembryonic cytokine-secreting cells (herein referred to as ECS cells), including, but not limited to, Amnion-derived Multipotent Progenitor cells (herein referred to as AMP cells) and conditioned media derived therefrom (herein referred to as Amnion-derived Cellular Cytokine Solution or ACCS), and Physiologic Cytokine Solution (herein referred to as PCS), each alone or in combination with each other and/or other agents.

18 Claims, No Drawings

METHODS FOR TREATING DENTAL DISEASES, DISORDERS, AND INJURIES

CROSS-REFERENCE TO RELATED APPLICATIONS

This application claims priority under 35 USC §119(e) of U.S. Provisional Application No. 61/459,859, filed Dec. 20, 2010, the entirety of which is incorporated herein by reference.

FIELD OF THE INVENTION

The field of the invention is directed to methods for preventing, reversing, ameliorating or treating dental diseases, disorders and injuries. In particular, the field of the invention is directed to preventing, reversing, ameliorating or treating dental diseases, disorders or injuries of the gingival (gums) and bone. Such methods for preventing, reversing, ameliorating and treating such dental diseases, disorders and injuries utilize novel compositions including extraembryonic cytokine-secreting cells (herein referred to as ECS cells) and conditioned medium derived therefrom, including Amnion-derived Multipotent Progenitor (AMP) cells, conditioned medium derived therefrom (herein referred to as Amnion-derived Cellular Cytokine Solution or ACCS, pooled ACCS), and/or cell products derived therefrom, and Physiologic Cytokine Solution (herein referred to as PCS), each alone and/or in combination with each other and/or with other agents including active and/or inactive agents.

BACKGROUND OF THE INVENTION

Gingivitis (inflammation of the gums) usually precedes periodontitis (gum disease). In the early stage of gingivitis, bacteria in plaque (a sticky, colorless film of bacteria that forms on teeth) causes the gums to become inflamed, often bleeding. At this stage the teeth are still firmly embedded in their sockets and no irreversible bone or other tissue damage has occurred. However, if left untreated, gingivitis can advance to periodontitis. In periodontitis, the inner layer of the gum and bone pull away from the teeth and form spaces called pockets. These pockets collect debris and often become infected. Toxins, which are produced by the bacteria in plaque, and enzymes produced by the body as it fights the infection, cause the breakdown of the bone and connective tissue that anchors the teeth. As the disease progresses, the pockets deepen and more bone and connective tissue are destroyed. Eventually the teeth are no longer anchored in place and become loose, often leading to tooth loss. In fact, periodontitis is the leading cause of tooth loss in adults.

Plaque is the primary cause of gingivitis and periodontitis. However, other factors can contribute to these diseases as well, including hormonal changes associated with pregnancy, puberty, menstruation, and menopause, all of which can make gums more sensitive and easier for gingivitis to develop. In addition, many illnesses can affect the gums. Such illnesses include diseases such as cancer or HIV infection, both of which can interfere with the proper functioning of the immune system. Diabetics are at generally at a higher risk of developing infections than non-diabetics, including periodontal disease. Medications can also affect oral health because some can decrease the flow of saliva, which has a protective effect on the teeth and gums. Smoking makes it harder for gum tissue to repair itself. And of course poor oral hygiene such as not brushing and flossing on a daily basis makes it easier for gingivitis to develop. A family history (genetics) of dental disease can be a contributing factor for the development of gum disease, as well.

Researchers have identified potential links between gum disease and other serious health conditions such as stroke and heart disease. Diabetes is not only a risk factor for gum disease, but gum disease may make diabetes worse.

Current non-surgical treatments for gum disease include professional dental cleaning to remove the plaque and tartar, which is plaque that builds up and hardens on the tooth surface, from above and below the gum line. Often a professional dental cleaning is recommended more than twice-a-year. Scaling and root planning are deep-cleaning, nonsurgical procedures done under a local anesthetic, whereby plaque and tartar from above and below the gum line are scraped away (scaling) and rough spots on the tooth root are made smooth (planing). Smoothing the rough spots removes bacteria and provides a clean surface for the gums to reattach to the teeth.

Surgical treatments for gum disease include flap surgery/pocket reduction surgery. During this procedure the gums are lifted back and the tarter is removed. In some cases, irregular surfaces of the damaged bone are smoothed to limit areas where disease-causing bacteria can accumulate. The gums are then placed so that the tissue fits snugly around the tooth. This method reduces the size of the pockets between the gum and tooth, thereby decreasing the areas where harmful bacteria can grow. Bone grafts involve using fragments of the patients own bone, synthetic bone, or donated bone to replace bone destroyed by gum disease. The grafts serve as a platform for the regrowth of bone, which restores stability to the teeth. New technology, called tissue engineering, encourages the body to regenerate bone and tissue at an accelerated rate. Soft tissue grafts reinforce thin gums or fills in areas where gums have receded. Grafted tissue, most often taken from the roof of the mouth, is sutured in place, adding tissue to the affected area. Guided tissue regeneration is performed when the bone supporting the teeth has been destroyed. This procedure stimulates bone and gum tissue growth. Done in combination with flap surgery, a small piece of mesh-like fabric is inserted between the bone and gum tissue. This keeps the gum tissue from growing into the area where the bone should be, allowing the bone and connective tissue to regrow to better support the teeth. Bone surgery smoothes shallow craters in the bone due to moderate and advanced bone loss. Following flap surgery, the bone around the tooth is reshaped to decrease the craters. This makes it harder for bacteria to collect and grow.

Antibiotic therapy can be used either in combination with surgery and other therapies, or alone, to reduce or temporarily eliminate the bacteria associated with gum disease or suppress the destruction of the tooth's attachment to the bone. Chlorhexidine is an antimicrobial used to control plaque and gingivitis in the mouth or in periodontal pockets. It is available as a mouth rinse or as a gelatin-filled chip that is placed in the pockets after root planing and releases the medication slowly over time. Other antibiotics, including doxycycline, tetracycline, and minocycline may also be used to treat gum disease. In addition, a nonprescription toothpaste that contains fluoride and an antibiotic to reduce plaque and gingivitis, called triclosan, may be recommended.

It is an object of the instant invention to provide novel treatment options for patients suffering from dental diseases, disorders or injuries, in particular, periodontal (gum) diseases, using the novel compositions described herein. It is also an object of the invention to provide novel treatment options for patients having other dental disorders or conditions such as oral ulcers, including viral ulcers, dental implants, bone grafts, factures of the bone, etc.

BRIEF SUMMARY OF THE INVENTION

It is an object of the instant invention to provide novel methods for preventing, reversing, ameliorating or treating dental diseases, disorders and injuries, in particular, periodontal (gum) diseases. Such methods for preventing, reversing, ameliorating and treating such dental diseases, disorders and injuries utilize novel compositions including extraembryonic cytokine-secreting cells (herein referred to as ECS cells) and conditioned medium derived therefrom, including Amnion-derived Multipotent Progenitor (AMP) cells, conditioned medium derived therefrom (herein referred to as Amnion-derived Cellular Cytokine Solution or ACCS, pooled ACCS), and/or cell products derived therefrom, and Physiologic Cytokine Solution (herein referred to as PCS), each alone and/or in combination with each other and/or with other agents including active and/or inactive agents.

Accordingly, a first aspect of the invention is a method for preventing, reversing, ameliorating or treating a dental disease, disorder or injury in a patient in need thereof comprising administering to the patient a therapeutically effective amount of one or more compositions selected from the group consisting of extraembryonic cytokine-secreting (ECS) cells, conditioned medium derived therefrom, cell lysate derived therefrom, cell products derived therefrom, and Physiologic Cytokine Solution (PCS).

In one embodiment of aspect 1 the dental disease is selected from the group consisting of gingivitis and periodontitis.

In another embodiment of aspect 1 the ECS cells are Amnion-derived Multipotent Progenitor (AMP) cells.

In yet another embodiment of aspect 1 the conditioned medium is Amnion-derived Cellular Cytokine Solution (ACCS) or pooled ACCS. In a specific embodiment, the ACCS or pooled ACCS is formulated for sustained-release.

In another specific embodiment of aspect 1 the PCS is formulated for sustained-release.

In still another embodiment of aspect 1 the ECS cells, conditioned medium derived therefrom, cell lysate derived therefrom or cell products derived therefrom are administered in combination with other agents or treatment modalities. In a specific embodiment, the other agents are active agents. In a particular embodiment the active agents are selected from the group consisting of growth factors, cytokines, inhibitors, immunosuppressive agents, steroids, chemokines, antibodies, antibiotics, antifungals, antivirals, mitomycin C, and other cell types. In another specific embodiment the other treatment modalities are selected from the group consisting of non-surgical and surgical treatment modalities. In a particular embodiment the nonsurgical treatment modalities are selected from the group consisting of professional dental cleaning, scaling and root planning. In a particular embodiment the surgical treatment modalities are selected from the group consisting of flap surgery/pocket reduction surgery, bone grafts, tissue engineering, soft tissue grafts, guided tissue regeneration, and bone surgery.

Other features and advantages of the invention will be apparent from the accompanying description, examples and the claims. The contents of all references, pending patent applications and issued patents, cited throughout this application are hereby expressly incorporated by reference. In case of conflict, the present specification, including definitions, will control.

Definitions

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of a cell or cell population. The protein marker may be located on the plasma membrane of a cell or in some cases may be a secreted protein.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cells" or "EE cells" means a population of cells derived from the extraembryonic tissue.

As used herein, the term "extraembryonic cytokine-secreting cells" or "ECS cells" means a population of cells derived from the extraembryonic tissue which have the characteristic of secreting VEGF, Angiogenin, PDGF and TGFβ2 and the MMP inhibitors TIMP-1 and/or TIMP-2 at physiologically relevant levels in a physiologically relevant temporal manner into the extracellular space or into the surrounding culture media. ECS cells have not been cultured in the presence of any non-human animal materials, making them and cell products derived from them suitable for human clinical use as they are not xeno-contaminated. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. Nos. 11/333,849, 11/392,892, PCTUS06/011392, US2006/0078993, PCT/US00/40052, U.S. Pat. No. 7,045,148, US2004/0048372, and US2003/0032179, the contents of which are incorporated herein by reference in their entirety. ECS cells were previously called trophic factor-secreting extraembryonic cells or TSE cells.

As used herein, the term "Amnion-derived Multipotent Progenitor cell" or "AMP cell" means a specific population of cells that are epithelial cells derived from the amnion. AMP cells have the following characteristics. They have not been cultured in the presence of any non-human animal materials, making them and cell products derived from them suitable for human clinical use as they are not xeno-contaminated. AMP cells are cultured in basal medium supplemented with human serum albumin. In a preferred embodiment, the AMP cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 μg/mL for TIMP-1 and ~1.04 μg/mL for TIMP-2. The AMP cells may optionally express Thymosin β4. AMP cells grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells, from which AMP cells are selected and isolated, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved and unique compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of amnion epithelial cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of amnion epithelial cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, the term "differentiation" means the process by which cells become progressively more specialized.

As used herein, the term "differentiation efficiency" means the percentage of cells in a population that are differentiating or are able to differentiate.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium.

As used herein, the term "Amnion-derived Cellular Cytokine Solution" or "ACCS" means conditioned medium that has been derived from AMP cells that have been cultured in basal media supplemented with human serum albumin. ACCS has previously been referred to as "amnion-derived cellular cytokine suspension".

The term "physiological level" as used herein means the level that a substance in a living system is found and that is relevant to the proper functioning of a biochemical and/or biological process.

As used herein, the term "Physiologic Cytokine Solution" or "PCS" composition means a composition which is not cell-derived and which has physiologic concentrations of one or more factors selected from VEGF, Angiogenin, PDGF and TGFβ2 and at least one MMP inhibitor. Examples of suitable MMP inhibitors include but are not limited to TIMP-1 and TIMP-2. Details on PCS can be found in U.S. Publication No. US-2009-0054339-A1, the contents of which are incorporated herein by reference.

As used herein, the term "pooled" means a plurality of compositions that have been combined to create a new composition having more constant or consistent characteristics as compared to the non-pooled compositions.

The term "therapeutically effective amount" means that amount of a therapeutic agent necessary to achieve a desired physiological effect (i.e. treat dental disease).

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In some instances, it may be desirable to lyse the cells and retain the cellular membrane portion and discard the remaining portion of the lysed cells.

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

The term "transplantation" as used herein refers to the administration of a composition comprising cells, including a cell suspension or cells incorporated into a matrix or tissue, that are either in an undifferentiated, partially differentiated, or fully differentiated form into a human or other animal.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease. The term "ameliorate" as used herein means to improve, make better, make more tolerable or reverse a condition, for example, a dental disease, disorder or injury.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses—The compositions of the invention are useful in preventing, reversing, ameliorating or treating dental diseases, disorders, or injuries, including but not limited to gingivitis and periodontitis.

Obtaining and Culturing of Cells

ECS cells—Various methods for isolating cells from the extraembryonic tissue, which may then be used to produce the ECS cells of the instant invention are described in the art (see, for example, US2003/0235563, US2004/0161419, US2005/0124003, U.S. Provisional Application Nos. 60/666, 949, 60/699,257, 60/742,067, 60/813,759, U.S. application Ser. Nos. 11/333,849, 11/392,892, PCTUS06/011392, US2006/0078993, PCT/US00/40052, U.S. Pat. No. 7,045, 148, US2004/0048372, and US2003/0032179).

Identifying ECS cells—Once extraembryonic tissue is isolated, it is necessary to identify which cells in the tissue have the characteristics associated with ECS cells (see definition above). For example, cells are assayed for their ability to secrete VEGF, Angiogenin, PDGF and TGFβ2 and the MMP inhibitors TIMP-1 and/or TIMP-2 into the extracellular space or into surrounding culture media. In some instances, it may be difficult or impossible to detect certain factors using standard assays. This may be because certain factors are secreted by the cells at physiological levels that are below the level of detection by the assay methods. It may also be that the factor (s) is being utilized by the ECS cell and/or by other local cells, thus preventing accumulation at detectable levels using standard assays. It is also possible that the temporal manner in which the factors are secreted may not coincide with the timing of sampling.

AMP cell compositions are prepared using the steps of a) recovery of the amnion from the placenta, b) dissociation of the epithelial cells from the amniotic membrane using a protease, c) culturing of the cells in a basal medium with the addition of a naturally derived or recombinantly produced human serum albumin and no non-human animal protein; d) selecting AMP cells from the epithelial cell culture, and optionally e) further proliferation of the cells, optionally using additional additives and/or growth factors (i.e. recombinant human EGF). Details are contained in US Publication No. 2006-0222634-A1, which is incorporated herein by reference.

Culturing of the AMP cells—The cells are cultured in a basal medium. Such medium includes, but is not limited to, EPILIFE® culture medium for epithelial cells (Cascade Biologicals), OPTI-PRO™ serum-free culture medium, VP-SFM serum-free medium, IMDM highly enriched basal medium, KNOCKOUT™ DMEM low osmolality medium, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium (all made by Cambrex), STEMLINE® T-cell expansion medium and STEMLINE® II hematopoietic stem cell expansion medium (both made by Sigma-Aldrich), DMEM culture medium, DMEM/F-12 nutrient mixture growth medium (both made by Gibco), Ham's F-12 nutrient mixture growth medium, M199 basal culture medium (both made by Sigma-Aldrich), and other comparable basal media. Such media should either contain human protein or be supplemented with human protein. As used herein a "human protein" is one that is produced naturally or one that is produced using recombinant technology, for example, human serum albumin. In specific embodiments, the basal media is IMDM highly enriched basal medium, STEMLINE® T-cell expansion medium or STEMLINE® II hematopoietic stem cell expansion medium, or OPTI-PRO™ serum-free culture medium, or combinations thereof and the human protein is human serum albumin added at at least 0.5% and up to 10%. In particular embodiments, the human serum albumin is from about 0.5% to about 2%. In a specific embodiment the human serum albumin is at 0.5%. The human serum albumin may come from a liquid or a dried (powder) form and includes, but is not limited to, recombinant human serum albumin, PLASBUMIN® normal human serum albumin and PLASMANATE® human blood fraction (both made by Talecris Biotherapeutics).

In a most preferred embodiment, the cells are cultured using a system that is free of non-human animal products to avoid xeno-contamination. In this embodiment, the culture medium is IMDM highly enriched basal medium, STEMLINE® T-cell expansion medium or STEMLINE® II hematopoietic stem cell expansion medium, OPTI-PRO™ serum-free culture medium, or DMEM culture medium, with human serum albumin added up to amounts of 10%.

The invention further contemplates the use of any of the above basal media wherein animal-derived proteins are replaced with recombinant human proteins and animal-derived serum, such as BSA, is replaced with human serum albumin. In preferred embodiments, the media is serum-free in addition to being non-human animal-free.

Optionally, other factors are used. In one embodiment, epidermal growth factor (EGF) at a concentration of between 0-1 μg/mL is used. In a preferred embodiment, the EGF concentration is around 10-20 ng/mL.

Generation of Conditioned Medium

ECS cell conditioned medium—is obtained as described below for ACCS, except that ECS cells are used.

Generation of ACCS—The AMP cells of the invention can be used to generate ACCS. In one embodiment, the AMP cells are isolated as described herein and $1 \times 10^6$ cells/mL are seeded into T75 flasks containing between 5-30 mL culture medium, preferably between 10-25 mL culture medium, and most preferably about 10 mL culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 3 days post-confluence. In another embodiment the medium is changed and ACCS is collected 4 days post-confluence. In another embodiment the medium is changed and ACCS is collected 5 days post-confluence. In another embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated that ACCS be formulated for sustained-release after collection.

The compositions of the invention can be prepared in a variety of ways depending on the intended use of the compositions. For example, a composition useful in practicing the invention may be a liquid comprising an agent of the invention, i.e. ECS cells, including AMP cells and/or ACCS, pooled ACCS or PCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions—The present invention provides pharmaceutical compositions of ECS cells, including AMP cells and/or ACCS, pooled ACCS or PCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—The invention also provides for an article of manufacture comprising packaging material and a pharmaceutical composition of the invention contained within the packaging material, wherein the pharmaceutical composition comprises compositions of ECS cells, including AMP cells and/or ACCS, pooled ACCS or PCS. The packaging material comprises a label or package insert which indicates that the ECS cells, including AMP cells and/or ACCS, pooled ACCS or PCS can be used for preventing, reversing, ameliorating or treating dental diseases, disorders or injuries.

Formulation, Dosage and Administration

Compositions comprising ECS cells, including AMP cells and/or ACCS, pooled ACCS or PCS may be administered to a subject to provide various cellular or tissue functions, for example, to prevent, reverse, ameliorate or treat dental diseases, disorders or injuries. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in preventing, reversing or treating dental diseases or restoring a therapeutically important metabolic function. The compositions may also be administered to the recipient in one or more physiologically acceptable carriers. Carriers for the cells may include but are not limited to solutions of phosphate buffered saline (PBS) or lactated Ringer's solution containing a mixture of salts in physiologic concentrations.

Pharmaceutical compositions useful in the practice of certain embodiments of the invention (i.e. those utilizing topical administration) include a therapeutically effective amount of an active agent with a pharmaceutically acceptable carrier. Such pharmaceutical compositions may be liquid, gel, ointment, salve, sustained-release formulations or other formulations suitable for administration to the gums, bone and teeth. The composition comprises a composition of the invention (i.e. ECS cells, including AMP cells and/or ACCS, pooled ACCS or PCS) and, optionally, at least one pharmaceutically acceptable excipient.

In various embodiments, compositions of the invention can comprise a liquid comprising an active agent in solution, in suspension, or both. The term "suspension" herein includes a liquid composition wherein a first portion of the active agent is present in solution and a second portion of the active agent is present in particulate form, in suspension in a liquid matrix. As used herein, liquid compositions include gels.

Preferably the liquid composition is aqueous. Alternatively, the composition can take form of an ointment. In a preferred embodiment, the composition is an in situ gellable aqueous composition, more preferably an in situ gellable aqueous solution. Such a composition can comprise a gelling agent in a concentration effective to promote gelling upon contact with the gums and/or teeth. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums. The phrase "in situ gellable" includes not only liquids of low viscosity that can form gels, but also more viscous liquids such as semi-fluid and thixotropic gels that exhibit substantially increased viscosity or gel stiffness upon administration.

Aqueous compositions of the invention have physiologically compatible pH and osmolality. Preferably these compositions incorporate means to inhibit microbial growth, for example through preparation and packaging under sterile conditions and/or through inclusion of an antimicrobially effective amount of an acceptable preservative. Suitable preservatives non-restrictively include mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

The composition can comprise a depot formulation comprising an active agent for topical administration. The depot formulation comprises a composition of the invention (i.e. ECS cells, including AMP cells and/or ACCS, pooled ACCS or PCS). The microparticles comprising the compositions can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

The composition can comprise a solid article that can be inserted in a suitable location in the mouth, where the article releases the active agent. Release from such an article is preferably to the teeth, gums and bone, with which the solid article is generally in intimate contact. Solid articles suitable for implantation in the mouth in such fashion generally comprise polymers and can be bioerodible or non-bioerodible. Bioerodible polymers that can be used in preparation of implants carrying a composition in accordance with the present invention include without restriction aliphatic polyesters such as polymers and copolymers of poly(glycolide), poly(lactide), poly(.epsilon.-caprolactone), poly(hydroxybutyrate) and poly(hydroxyvalerate), polyamino acids, polyorthoesters, polyanhydrides, aliphatic polycarbonates and polyether lactose. Illustrative of suitable non-bioerodible polymers are silicone elastomers.

One of skill in the art may readily determine the appropriate concentration, or dose, of the ECS cells, including AMP cells and/or ACCS, pooled ACCS or PCS, for a particular purpose. The skilled artisan will recognize that a preferred dose is one which produces a therapeutic effect, such as preventing, reversing, ameliorating or treating dental diseases, disorders or injuries in a patient in need thereof. For example, one preferred dose of ACCS, pooled ACCS or PCS is in the range of about 0.1-to-1000 µL per square centimeter of applied area. Other preferred dose ranges are 1.0-100 µL per square centimeter of applied area and about 0.01-to-50.0 µL per square centimeter of applied area. Likewise, ECS cells, including AMP cells, are prepared at a concentration of between about $1\times10^7$–$1\times10^8$ cells/mL, preferably at about $2.5\times10^7$–$7.5\times10^7$ cells/mL, and most preferably at about $5 \times 10^7$ cells/mL. Of course, proper doses of the ECS cells, including AMP cells and/or ACCS, pooled ACCS or PCS, will require empirical determination at time of use based on several variables including but not limited to the severity and type of disease, injury, disorder or condition being treated; patient age, weight, sex, health; other medications and treatments being administered to the patient; and the like. One of skill in the art will also recognize that number of doses (dosing regimen) to be administered needs also to be empirically determined based on, for example, severity and type of disease, injury, disorder or condition being treated. In a preferred embodiment, one dose is sufficient. Other preferred embodiments contemplate, 2, 3, 4, or more doses.

In further embodiments of the present invention, it may be desirable to co-administer other agents, including active agents and/or inactive agents, with the ECS cells, including AMP cells and/or ACCS, pooled ACCS or PCS, to prevent, reverse, ameliorate or treat dental diseases. Active agents include but are not limited to cytokines, chemokines, antibodies, inhibitors, antibiotics, anti-fungals, anti-virals, immunosuppressive agents, other cell types, and the like. Inactive agents include carriers, diluents, stabilizers, gelling agents, delivery vehicles, ECMs (natural and synthetic), scaffolds, and the like. When the ECS cells, including AMP cells and/or ACCS, pooled ACCS or PCS, are administered conjointly with other pharmaceutically active agents, even less of the ECS cells, including AMP cells and/or ACCS, pooled ACCS or PCS, may be needed to be therapeutically effective.

ECS cells, including AMP cells and/or ACCS, pooled ACCS or PCS, can be administered by injection into a target site of a subject, preferably via a delivery device, such as a tube, e.g., catheter. In a preferred embodiment, the tube additionally contains a needle, e.g., a syringe, through which the cells and/or ACCS or PCS can be introduced into the subject at a desired location.

The timing of administration of ECS cells, including AMP cells and/or ACCS, pooled ACCS or PCS, will depend upon the type and severity of the dental disease being treated. In a preferred embodiment, the ECS cells, including AMP cells and/or ACCS, pooled ACCS or PCS, are administered as soon as possible after the dental disease is diagnosed. In other preferred embodiments, the ECS cells, including AMP cells and/or ACCS, pooled ACCS or PCS, are administered more than one time following diagnosis.

Also contemplated by the methods of the invention are compositions comprising cells that have been partially or fully differentiated. Such partially or fully differentiated cell compositions are obtained by treating ECS cells, including AMP cells, with appropriate reagents and under appropriate conditions wherein the cells undergo partial or complete differentiation into, for example, connective tissue cells such as, for example, fibroblasts or bone cells. Skilled artisans are familiar with conditions capable of effecting such partial or complete differentiation. The cells may be treated under differentiating conditions prior to use (i.e. prior to transplantation, administration, etc.) or simultaneously with use. In certain embodiments, the cells are treated under differentiation conditions before and during use.

Sustained-Release Compositions

The ACCS, pooled ACCS or PCS, maybe formulated as sustained-release compositions. Skilled artisans are familiar with methodologies to create sustained-release compositions of therapeutic agents, including protein-based therapeutic agents such as ACCS, pooled ACCS or PCS.

The sustained-release compositions may be made by any of the methods described herein. For example, multivesicular liposome formulation technology is useful for the sustained-release of protein and peptide therapeutics. Qui, J., et al, (ACTA Pharmacol Sin, 2005, 26(11):1395-401) describe this methodology for the formulation of sustained-release interferon alpha-2b. Vyas, S. P., et al, (Drug Dev Ind Pharm, 2006, 32(6):699-707) describe encapsulating pegylated interferon alpha in multivesicular liposomes. ACCS, including pooled ACCS, and PCS are suitable for use in multivesicular liposome sustained-release formulation.

Nanoparticle technology is also useful for creating sustained-release compositions. For example, Packhaeuser, C. B., et al, (J Control Release, 2007, 123(2):131-40) describe biodegradable parenteral depot systems based on insulin loaded dialkylaminoalkyl-amine-poly(vinyl alcohol)-g-poly (lactide-co-glycolide) nanoparticules and conclude that nanoparticle-based depots are suitable candidates for the design of controlled-release devices for bioactive macromolecules (i.e. proteins). Dailey, L. A., et al, (Pharm Res 2003, 20(12):2011-20) describe surfactant-free, biodegradable nanoparticles for aerosol therapy which is based on the branched polymers DEAPA-PVAL-g-PLGA and conclude that DEAPA-PVAL-g-PLGA are versatile drug delivery systems. ACCS, including pooled ACCS, and PCS are suitable for use in nanoparticle-based sustained-release formulations.

Polymer-based sustained-release formulations are also very useful. Chan, Y. P., et al, (Expert Opin Drug Deliv, 2007, 4(4):441-51) provide a review of the Medusa system (Flamel Technologies), which is used for sustained-release of protein and peptide therapies. Thus far, the Medusa system has been applied to subcutaneous injection of IL-2 and IFN-alpha(2b), in animal models (rats, dogs, monkeys), and in clinical trials in renal cancer (IL-2) and hepatitis C (IFN-alpha(2b)) patients. Chavanpatil, M. D., et al, (Pharm Res, 2007, 24(4): 803-10) describe surfactant-polymer nanoparticles as a novel platform for sustained and enhanced cellular delivery of water-soluble molecules. Takeuchi, H., et al, (Adv Drug Deliv Res, 2001, 47(1):39-54) describe mucoadhesive nanoparticulate systems for peptide drug delivery, including liposomes and polymeric nanoparticles. Wong, H. L., et al, (Pharm Res, 2006, 23(7):1574-85) describe a new polymer-lipid hybrid system which has been shown to increase cytotoxicity of doxorubicin against multidrug-resistant breast cancer cells. ACCS, including pooled ACCS, and PCS are suitable for use in the aforementioned sustained-release formulation methodologies.

In addition, other sustained-release methodologies familiar to skilled artisans, while not specifically described herein, are also suitable for use.

Skilled artisans will recognize that any and all of the standard methods and modalities for preventing, reversing or treating dental diseases currently in clinical practice and clinical development are suitable for practicing the methods of the invention. Routes of administration, formulation, co-administration with other agents (if appropriate) and the like are discussed in detail elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of AMP Cell Compositions

Amnion epithelial cells were dissociated from starting amniotic membrane using the dissociation agents PXXIII. The average weight range of an amnion was 18-27 g. The number of cells recovered per g of amnion was about 10-15× $10^6$ for dissociation with PXXIII.

Method of obtaining selected AMP cells—Amnion epithelial cells were plated immediately upon isolation from the amnion. After ~2 days in culture non-adherent cells were removed and the adherent cells were kept. This attachment to a plastic tissue culture vessel is the selection method used to obtain the desired population of AMP cells. Adherent and non-adherent AMP cells appear to have a similar cell surface marker expression profile but the adherent cells have greater viability and are the desired population of cells. Adherent AMP cells were cultured in basal medium supplemented with human serum albumin until they reached ~120,000-150,000 cells/cm². At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached ~120,000-150,000 cells/cm², they were collected and cryopreserved. This collection time point is called p0.

Example 2

Generation of ACCS

The AMP cells of the invention can be used to generate ACCS, including pooled ACCS. The AMP cells were isolated as described above and ~1×10⁶ cells/mL were seeded into T75 flasks containing ~10 mL culture medium as described above. The cells were cultured until confluent, the medium was changed and ACCS was collected 3 days post-confluence. Optionally, the ACCS is collected again after 3 days, and optionally again after 3 days. Skilled artisans will recognize that other embodiments for collecting ACCS from confluent cultures, such as using other tissue culture vessels, including but not limited to cell factories, flasks, hollow fibers, or suspension culture apparatus, etc. are also contemplated by the methods of the invention (see Detailed Description above). It is also contemplated by the instant invention that the ACCS be cryopreserved, lyophilized, irradiated and/or formulated for sustained-release following collection. It is also contemplated that ACCS be collected at different time points (see Detailed Description for details).

Example 3

Generation of PCS Compositions

The following PCS compositions are produced by combining the indicated cytokine or factor at physiologic levels in a carrier:

Composition A: VEGF and TIMP-1; Composition B: VEGF, Angiogenin and TIMP-1; Composition C: VEGF, Angiogenin, PDGF-BB and TIMP-1; Composition D: VEGF, Angiogenin, PDGF-BB, TGFβ2 and TIMP-1; Composition E: VEGF and TIMP-2; Composition F: VEGF, Angiogenin and TIMP-2; Composition G: VEGF, Angiogenin, PDGF-BB and TIMP-2; Composition H: VEGF, Angiogenin, PDGF-BB, TGFβ2 and TIMP-2; Composition I: VEGF, TIMP-1 and TIMP-2; Composition J: VEGF, Angiogenin, TIMP-1 and TIMP-2; Composition K: VEGF, Angiogenin, PDGF-BB, TIMP-1 and TIMP-2; Composition L: VEGF, Angiogenin, PDGF-BB, TGFβ2, TIMP-1 and TIMP-2; Composition M: Angiogenin and TIMP-1; Composition N: Angiogenin, PDGF-BB and TIMP-1; Composition O: Angiogenin, PDGF-BB, TGFβ2 and TIMP-1; Composition P: Angiogenin and TIMP-2; Composition Q: Angiogenin, PDGF-BB and TIMP-2; Composition R: Angiogenin, PDGF-BB, TGFβ2 and TIMP-2; Composition S: Angiogenin, PDGF-BB, TGFβ2, TIMP-1 and TIMP-2; Composition T: PDGF-BB and TIMP-1; Composition U: PDGF-BB, TGFβ2 and TIMP-1; Composition V: PDGF-BB and TIMP-2; Composition W: PDGF-BB, TGFβ2 and TIMP-2; Composition X: PDGF-BB, TIMP-1 and TIMP-2; Composition Y: PDGF-BB, TGFβ2, TIMP-1 and TIMP-2. A preferred composition is Composition L.

Compositions A-Y optionally contains Thymosin β4. Skilled artisans will recognize that in certain embodiments other MMP inhibitors (i.e. TIMP-3, TIMP-4 or synthetic MMP inhibitors) may be suitable (J. Frederick Woessner, Jr., J. Clin. Invest. 108(6): 799-800 (2001); Brew, K., et al, Biochim Biophys Acta. 2000 Mar. 7; 1477(1-2):267-83).

VEGF, Angiogenin, PDGF-BB, TGFβ2, TIMP-1 and TIMP-2 are added at the following physiologic levels: ~5-16 ng/mL for VEGF, —3.5-4.5 ng/mL for Angiogenin, —100-165 pg/mL for PDGF, ~2.5-2.7 ng/mL for TGFβ2, ~0.68 μg mL for TIMP-1 and ~1.04 μg/mL for TIMP-2. VEGF may be obtained from Invitrogen, catalog #PHG0144, PHG0145, PHG0146, PHG0141 or PHG0143; Angiogenin may be obtained from R&D Systems, catalog #265-AN-050 or 265-AN-250; PDGF-BB may be obtained from Invitrogen, catalog #PHG0044, #PHG0045, #PHG0046, #PHG0041, #PHG0043; TGFβ2 may be obtained from Invitrogen, catalog #PHG9114; TIMP-1 may be obtained from R&D Systems, catalog #970-TM-010; and TIMP-2 may be obtained from R&D Systems, catalog #971-TM-010. VEGF, Angiogenin, PDGF-BB, TGFβ2, TIMP-1 and TIMP-2 are added to a carrier such as normal saline, PBS, lactated Ringer's solution, cell culture media, water or other suitable aqueous solution known to skilled artisans.

Example 4

Generation of Sustained-Release Compositions

Sustained-release compositions of ACCS, including pooled ACCS, or PCS, are produced by combining ACCS, including pooled ACCS, or PCS compositions with any of the sustained-release formulation technologies described herein (see Detailed Description) or otherwise familiar to skilled artisans.

Example 5

Use of ACCS to Prevent Onset of Periodontal Disease in an Animal Model

Model: ACCS was tested in a rabbit model of *P. gingivalis*-induced periodontitis. The model utilized ligature+*P. gingivalis* application over a six week period which induces a considerable amount of gingival inflammation and bone loss associated with periodontal disease as the confirmation of the disease model. ACCS was applied prior to *P. gingivalis* application and then 3 times a week over the next 6 six weeks.

Results: Topical application of ACCS resulted in a significant level of protection from inflammatory changes in soft tissue and bone loss induced by ligature+*P. gingivalis*. These data indicate that ACCS can either prevent or ameliorate the onset of periodontal disease. Placebo (unconditioned medium) application did not have any protective action as indicated by a significant amount of soft tissue inflammation and bone loss which was similar to that seen in the untreated group.

Example 6

Use of ACCS to Stop Progression of or Reverse Periodontal Disease in an Animal Model Model: ACCS is tested in a rabbit model of *P. gingivalis*-induced periodontitis. The model utilizes ligature+*P. gingivalis* application over a six week period which induces a considerable amount of gingival inflammation and bone loss associated with periodontal disease as the confirmation of the disease model. ACCS is applied 6 weeks after ligature+*P. gingivalis* application and then 3 times a week over an additional 6 six weeks.

Example 7

Use of AMP Cells in an Animal Model of Periodontal Disease

Model: AMP cells are tested in a rabbit model of *P. gingivalis*-induced periodontitis. The model utilizes ligature+*P. gingivalis* application over a six week period which induces a considerable amount of gingival inflammation and bone loss associated with periodontal disease as the confirmation of the disease model. It is expected that AMP cells will have the same positive effect (prevent or reverse or stop progression of disease) as ACCS because AMP cells secrete the active factors present in ACCS.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for ameliorating or treating a dental disease, disorder or injury in a patient in need thereof, the method comprising the step of administering to the patient a therapeutically effective amount of Amnion-derived Cellular Cytokine Solution (ACCS) or pooled ACCS, wherein the ACCS or pooled ACCS comprises physiologic levels of VEGF, Angiogenin, PDGF, TGFIβ2, TIMP-1 and TIMP-2 that are dissolved in an aqueous solution, wherein the physiologic levels are ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2.

2. The method of claim 1 wherein the dental disease is selected from the group consisting of gingivitis and periodontitis.

3. The method of claim 1 wherein the ACCS or pooled ACCS are formulated for sustained-release.

4. The method of claim 1 wherein the ACCS or pooled ACCS are administered in combination with other agents or treatment modalities.

5. The method of claim 4 wherein the other treatment modalities are selected from the group consisting of non-surgical and surgical treatment modalities.

6. The method of claim 5 wherein the non-surgical treatment modalities are selected from the group consisting of professional dental cleaning, scaling, and root planning.

7. The method of claim 5 wherein the surgical treatment modalities are selected from the group consisting of flap surgery/pocket reduction surgery, bone grafts, tissue engineering, soft tissue grafts, guided tissue regeneration, and bone surgery.

8. The method of claim 4 wherein the other agents are active agents.

9. The method of claim 8 wherein the active agents are selected from the group consisting of growth factors, cytokines, inhibitors, immunosuppressive agents, steroids, chemokines, antibodies, antibiotics, antifungals, antivirals, mitomycin C, and other cell types.

10. A method for ameliorating or treating a dental disease, disorder or injury in a patient in need thereof, the method comprising the step of administering to the patient a therapeutically effective amount of Physiological Cytokine Solution (PCS), wherein the PCS consists of physiologic levels of VEGF, Angiogenin, PDGF, TGFβ2, TIMP-1 and TIMP-2 that are dissolved in an aqueous solution, wherein the physiologic levels are ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2.

11. The method of claim 10 wherein the dental disease is selected from the group consisting of gingivitis and periodontitis.

12. The method of claim 10 wherein the PCS is formulated for sustained-release.

13. The method of claim 10 wherein the PCS is administered in combination with other agents or treatment modalities.

14. The method of claim 13 wherein the other agents are active agents.

15. The method of claim 14 wherein the active agents are selected from the group consisting of growth factors, cytokines, inhibitors, immunosuppressive agents, steroids, chemokines, antibodies, antibiotics, antifungals, antivirals, mitomycin C, and other cell types.

16. The method of claim 13 wherein the other treatment modalities are selected from the group consisting of non-surgical and surgical treatment modalities.

17. The method of claim 16 wherein the non-surgical treatment modalities are selected from the group consisting of professional dental cleaning, scaling, and root planning.

18. The method of claim 16 wherein the surgical treatment modalities are selected from the group consisting of flap surgery/pocket reduction surgery, bone grafts, tissue engineering, soft tissue grafts, guided tissue regeneration, and bone surgery.

* * * * *